US011071655B2

(12) United States Patent
McCabe et al.

(10) Patent No.: US 11,071,655 B2
(45) Date of Patent: Jul. 27, 2021

(54) APPARATUS AND METHOD FOR HIGH SPEED CROSS FOLDING

(71) Applicant: Curt G. Joa, Inc., Sheboygan Falls, WI (US)

(72) Inventors: John A. McCabe, Sheboygan Falls, WI (US); Gottfried Jason Hohm, Sheboygan Falls, WI (US); Anthony A. Nelson, New Holstein, WI (US); Zachary J. Giffey, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 149 days.

(21) Appl. No.: 16/358,778

(22) Filed: Mar. 20, 2019

(65) Prior Publication Data

US 2019/0216654 A1 Jul. 18, 2019

Related U.S. Application Data

(63) Continuation of application No. 14/162,399, filed on Jan. 23, 2014, now Pat. No. 10,792,196.

(51) Int. Cl.
*A61F 13/15* (2006.01)
*B65H 45/12* (2006.01)

(52) U.S. Cl.
CPC ....... *A61F 13/15747* (2013.01); *B65H 45/12* (2013.01); *B65H 2404/2321* (2013.01); *B65H 2404/62* (2013.01); *B65H 2801/57* (2013.01)

(58) Field of Classification Search
CPC ...... B65H 45/147; B65H 45/16; B65H 45/12; B65H 2404/2321; B65H 2404/62;
(Continued)

(56) References Cited

U.S. PATENT DOCUMENTS 3,572,689 A * 3/1971 Murphy ................. D06F 89/00
493/423
4,157,058 A * 6/1979 Vogel ..................... B65H 45/16
493/124
(Continued)

FOREIGN PATENT DOCUMENTS

WO 2012123813 A1 9/2012

OTHER PUBLICATIONS

Supplementary European Search Report dated Sep. 21, 2017 regarding EP Appl. No. 14880017.0, 5 pages.
(Continued)

*Primary Examiner* — Dariush Seif
(74) *Attorney, Agent, or Firm* — Ziolkowski Patent Solutions Group, SC (57) ABSTRACT

Apparatus and methods are provided for folding discrete items such as diapers at high speeds. Discrete items are conveyed in a machine direction toward a pair of engaging members rotating in the machine direction and first carrying a top side of a leading edge of the discrete item with a first engaging member away from the conveyor, and then carrying a bottom side of the leading edge with a second engaging member back towards the conveyor. The diaper fold is created at a contact point with a folding finger which travels rotationally and straight in a fixed orientation about a travel path into and out of contact with the diaper.

24 Claims, 13 Drawing Sheets (58) Field of Classification Search
CPC .. B65H 2801/57; B31F 1/30; A61F 13/15747; B32B 2555/02
USPC ....... 493/416, 418, 422, 423, 424, 425, 427, 493/434, 435, 438, 442, 450
See application file for complete search history.

(56) References Cited

U.S. PATENT DOCUMENTS

| | | | |
|---|---|---|---|
| 4,285,621 A * | 8/1981 | Spencer | B65H 29/38 414/790 |
| 4,360,194 A * | 11/1982 | Bradley | B65H 35/04 270/42 |
| 4,508,528 A * | 4/1985 | Hirsch | B65H 45/18 270/45 |
| 4,549,876 A * | 10/1985 | Baker | B31B 50/00 493/169 |
| 4,616,815 A | 10/1986 | Vijuk | |
| 4,717,375 A * | 1/1988 | Landmark | A61F 13/15747 493/357 |
| 4,938,739 A * | 7/1990 | Nilsson | B65H 45/20 493/422 |
| 5,074,547 A | 12/1991 | Smith et al. | |
| 5,152,734 A | 10/1992 | McAdam, III et al. | |
| 5,788,805 A * | 8/1998 | Herrmann | A61F 13/15577 156/443 |
| 5,795,433 A | 8/1998 | Niedermeyer | |
| 6,086,522 A * | 7/2000 | Hechler | B65H 45/147 493/18 |
| 6,514,187 B2 | 2/2003 | Coenen et al. | |
| 7,264,583 B2 * | 9/2007 | Gelli | B65H 45/28 493/430 |
| 7,384,386 B2 * | 6/2008 | Sosalla | A61F 13/15747 493/441 |
| 7,399,266 B2 * | 7/2008 | Aiolfi | A61F 13/15747 493/424 |
| 8,257,237 B2 | 9/2012 | Burns, Jr. et al. | |
| 8,439,814 B2 * | 5/2013 | Piantoni | A61F 13/15747 493/416 |
| 8,485,956 B2 | 7/2013 | Burns, Jr. et al. | |
| 8,617,040 B2 * | 12/2013 | Coenen | B65H 45/16 493/442 |
| 8,870,732 B2 * | 10/2014 | Schneider | A61F 13/15747 493/416 |
| 2004/0063559 A1 * | 4/2004 | Ochsenbauer | B65H 45/28 493/427 |
| 2005/0092440 A1 * | 5/2005 | Lindsay | B65H 45/144 156/442.1 |
| 2006/0276320 A1 * | 12/2006 | Aiolfi | B65B 63/045 493/441 |
| 2007/0129230 A1 | 6/2007 | Sosalla | |
| 2008/0026925 A1 * | 1/2008 | Allen | A61F 13/15747 493/423 |
| 2009/0094941 A1 * | 4/2009 | Burns, Jr. | B65H 45/14 53/429 |
| 2010/0263987 A1 * | 10/2010 | Meyer | A61F 13/15764 198/461.1 |
| 2011/0003673 A1 * | 1/2011 | Piantoni | B65H 45/16 493/416 |
| 2011/0251040 A1 * | 10/2011 | Yamamoto | B65H 45/167 493/418 |
| 2012/0088646 A1 * | 4/2012 | Berggren | A61F 13/15593 493/393 |
| 2012/0157282 A1 * | 6/2012 | Schneider | A61F 13/15747 493/379 |
| 2012/0157288 A1 * | 6/2012 | Coenen | B65H 45/16 493/435 |
| 2012/0302418 A1 * | 11/2012 | Burns, Jr. | A61F 13/15764 493/442 |
| 2013/0270065 A1 | 10/2013 | Papsdort et al. | |
| 2014/0171284 A1 | 6/2014 | Coenen et al. | |
| 2015/0111715 A1 * | 4/2015 | Kloft | B65H 45/12 493/450 |
| 2015/0202092 A1 * | 7/2015 | Mccabe | A61F 13/15747 493/416 |
| 2016/0194174 A1 * | 7/2016 | Schoulz | B65H 45/16 493/418 |

OTHER PUBLICATIONS

Extended European Search Report dated Jun. 24, 2019 regarding EP Application No. 18215765.1, 11 pages.

* cited by examiner

APPARATUS AND METHOD FOR HIGH SPEED CROSS FOLDING

CROSS-REFERENCE TO RELATED APPLICATION

The present application is a continuation of, and claims priority to, U.S. patent application Ser. No. 14/162,399, filed Jan. 23, 2014, the disclosure of which is incorporated herein by reference in its entirety.

BACKGROUND OF THE INVENTION

The invention disclosed herein relates to apparatus and methods for folding discrete pieces traveling on a production line. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

The diaper is built by sandwiching the formed core between a backsheet and a topsheet, and the combined web receives ears for securing the diaper about the waist of a baby.

Most products require some longitudinal folding. It can be combined with elastic strands to make a cuff. It can be used to overwrap a stiff edge to soften the feel of the product. It can also be used to convert the final product into a smaller form to improve the packaging.

Diapers are typically formed in a machine direction in a generally flat condition. Formed diapers require folding both longitudinally to tuck the ears and associated tape or hook applicators into the diaper, and also cross-folded generally at a crotch region to stack the diapers prior to packaging.

The folded product is then passed downstream to a packaging machine where the diapers are stacked and packaged and shipped for sale.

BRIEF DESCRIPTION OF THE INVENTION

Provided are method and apparatus for minimizing waste and improving quality and production in web processing operations.

Importantly, the methods taught in the present application are applicable not only to diapers and the like, but in any web-based operation. The folding techniques taught herein can be directed any discrete component of a manufactured article, i.e., the methods taught herein are not product specific. For instance, the present methods can be applied as easily with respect to diaper components as they can for feminine hygiene products.

Apparatus and methods are provided for folding discrete items such as diapers at high speeds. Discrete items are conveyed in a machine direction toward a pair of vacuum drums rotating in the machine direction and first carrying a top side of a leading edge of the discrete item away from the conveyor, and then carrying a bottom side of the leading edge with a second rotational vacuum drum back towards the conveyor. The diaper fold is created at a contact point with a folding finger which travels rotationally and straight in a fixed orientation about a pair of belts, into and out of contact with the diaper.

BRIEF DESCRIPTION OF THE DRAWINGS

FIGS. 4A and 4B, and likewise FIGS. 5A and 5B through FIGS. 14A and 14B are side views of the folding system of the present invention operating through an entire folding sequence, and the correlating top views of the operator and drive side blade advancement devices operating through an entire folding sequence.

DETAILED DESCRIPTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present folding techniques and apparatus are described herein with respect to products such as diapers, but as previously mentioned, can be applied to a wide variety of processes in which discrete components are applied sequentially.

Figure 1:
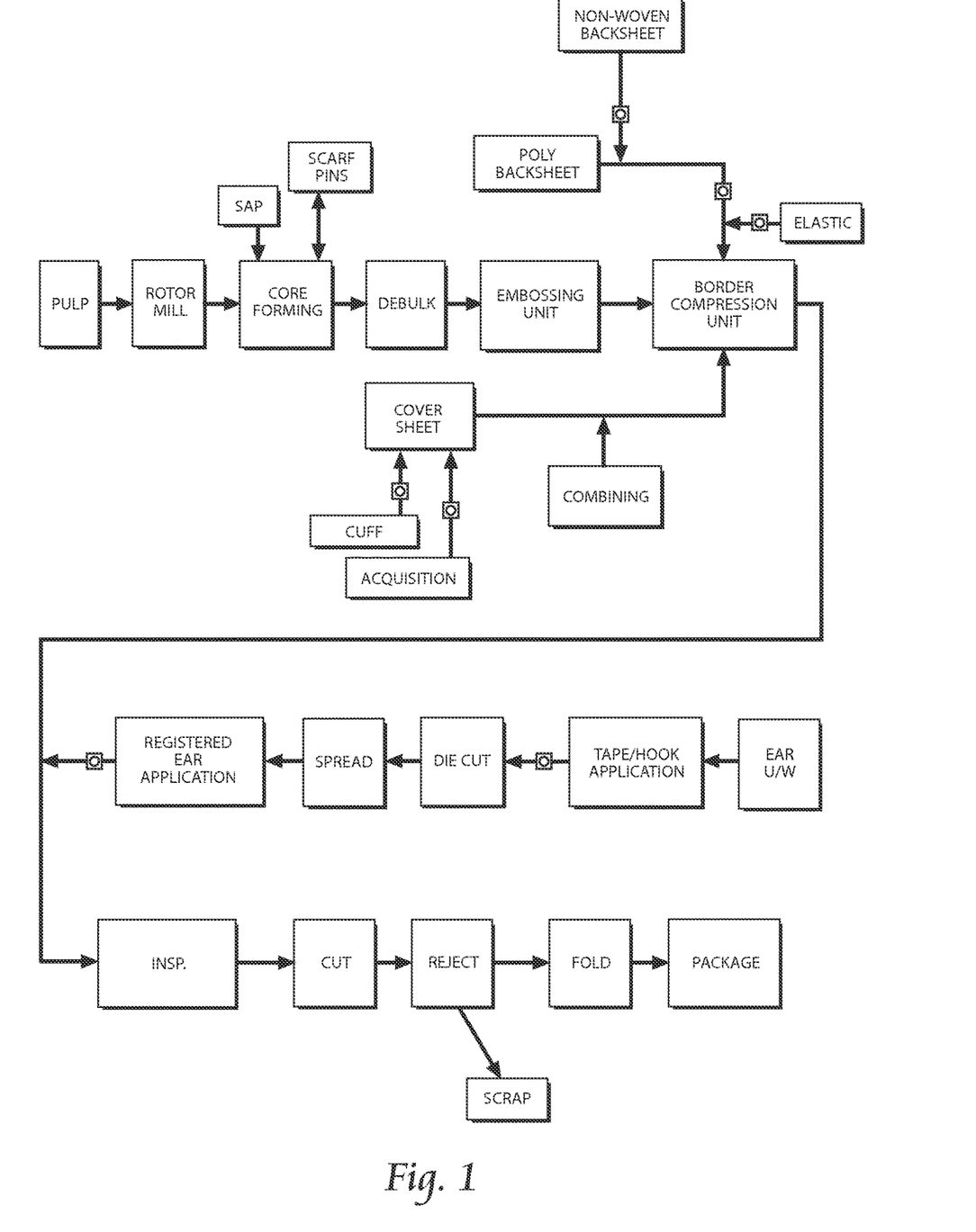
FIG. 1 is a schematic of a representative web processing system.

Referring to FIG. 1, a web processing operation starts with incorporating raw materials such as paper pulp and super absorbent polymer (SAP) in a pulp mill. The mixture is sent to a core forming drum, where cores are formed for retaining liquids. The core undergoes scarfing to trim the core to desired dimensions.

The process continues through debulking, embossing, optionally core cutting and spacing, and optionally, compression. The core can be placed between a preformed cover sheet containing cuff elastics and an acquisition layer, and a backsheet layer, sandwiching the core.

Ears are formed by applying a tape or hook and loop fastening mechanism to an ear web, and ears are die cut and spaced and spread as necessary, for instance as described in U.S. Pat. No. 8,016,972, incorporated herein by reference. The web can undergo folding, extraction and trimming of excess material, and application of material to tighten the diaper about the waist. Eventually, the product is folded and packaged.

As seen on FIG. 1, the symbol is shown at locations of introductions of discrete components into the process. At these locations, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

The present invention is directed at the folding step in the position indicated on FIG. 1. The device used to perform the folding step is described and shown with reference to the following figures and description.

Figure 2:
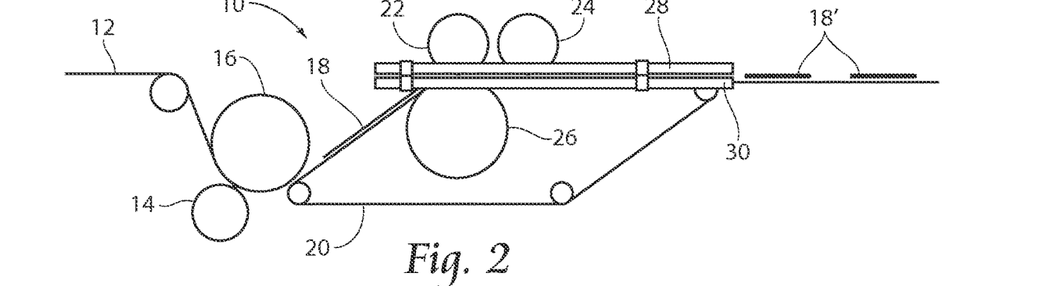
FIG. 2 is a side view of a folding system of the present invention.

Referring now to FIG. 2, a side view of a folding system 10 of the present invention is shown from an operator side of the folding system. An incoming web of material 12 to be folded enters a slip/cut anvil 14 and knife 16 combination to sever the web 12 into discrete pieces 18. The incoming web of material 12 can have ear segments already folded over as described with reference to FIG. 1.

After being severed into a single diaper (or other single discrete component) 18, the diaper is conveyed by a bottom feed conveyor 20 to a combination of vacuum drums 22, 24 and 26 which control movement and initiate the folding as will be described later. A pair of rotating belt units 28 and 30 rotate folding fingers 36 not visible from this view. The folding fingers tuck the diaper to support the folded diaper and the folded diapers 18' are passed downstream to stacking and packaging.

Figure 3A:
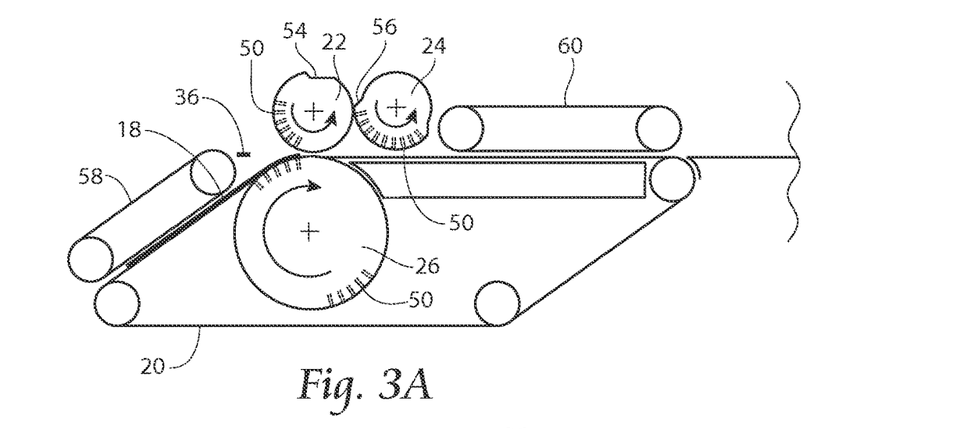
FIG. 3A is a side view of a folding system of the present invention at a beginning point of a folding sequence, with an operator and a drive side folding finger advancement device hidden.
Figure 3B:
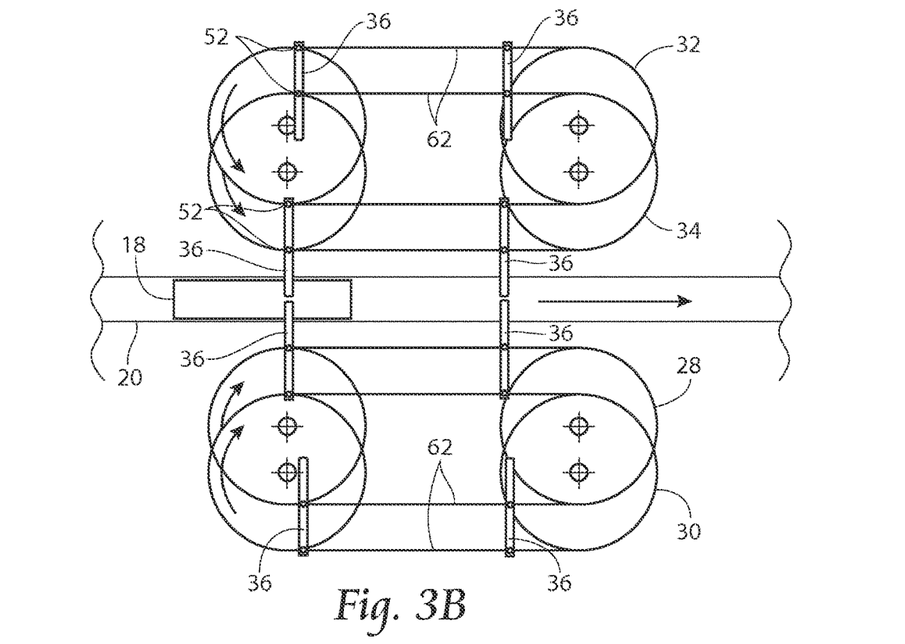
FIG. 3B is a top view of the operator and drive side blade advancement devices of the folding system, shown in sequence with FIG. 4A.

Referring now to FIG. 3A, a side view of the folding system 10 of the present invention at a beginning point of a folding sequence is shown. In this view for simplicity, the operator side rotating belt units 28 and 30, and drive side rotating belt units 32 and 34 are not shown. FIG. 3B is top view of the operator and drive side blade advancement devices of the folding system, shown in sequence with FIG. 3A. FIGS. 3A and 3B, and likewise FIGS. 4A and 4B-FIGS. 14A and 14B are side and top views respectively of the folding system of the present invention operating through an entire folding sequence of a single diaper 18. This sequence is intended to be carried out repeatedly and continuously on a continuous stream of incoming discrete diapers 18.

Referring still to FIG. 3A, a top feed conveyor 58 in conjunction with the bottom feed conveyor 20 transport diaper 18 from the anvil 16/knife 14 combination of FIG. 2. The diaper is carried by a first vacuum drum 26 provided with vacuum ports 50 to transport the diaper 18. A folding finger 36 can be seen approaching the laid out diaper between vacuum rolls 22 and 26, and travels horizontally just above the top horizontal surface of conveyor 20. For simplicity of illustration, a single folding finger 36 is shown in FIG. 3A and subsequent side views, but in a preferred embodiment, two folding fingers 36 will cooperate in tandem to assist in folding of diaper 18. It is noted that a single folding finger 36 could be used in the folding operation, in this embodiment only one tandem of the operator side rotating belt units 28 and 30, or drive side rotating belt units 32 and 34 would be necessary.

Vacuum drum 26 operates clockwise as shown, and vacuum drum 22 operates counterclockwise as shown from an operator side view. The construction and operation of high speed vacuum ported drums 22, 24 and 26 can be constructed according to the vacuum porting design and principles described in U.S. Pat. No. 7,533,709, incorporated herein by reference. In summary of that teaching, the vacuum ported drums 22, 24 and 26 are generally cylindrical bodies connected to a source of vacuum. The drums have a diaper retaining portion on their outer surfaces in order to hold (when desired) and control the path of the diaper 18. The diaper retaining portion is formed with a plurality of vacuum holes on the cylindrical surface. A vacuum slot (not shown) is provided on an end face surface (commutating surface) of the vacuum ported drums 22, 24 and 26 and is adapted to put the plurality of vacuum holes in communication with the vacuum source. In this manner, instantaneous on/off control of vacuum surface ports 50 can be achieved as described in U.S. Pat. No. 7,533,709.

Referring now to FIG. 3B, operator side rotating belt units 28 and 30, and drive side rotating belt units 32 and 34 are shown. Each of operator side rotating belt units 28 and 30, and drive side rotating belt units 32 and 34 the carry a belt 62, and each is rotated for instance by a motor (not shown). In the view shown, in conjunction with FIG. 3A, the operator side rotating belt units 28 and 30, and drive side rotating belt units 32 and 34 rotate counterclockwise to advance folding fingers 36 around the travel path of the belt units, with the folding fingers oriented to point upward for the operator side rotating belt units 28 and 30, and downward for drive side rotating belt units 32 and 34. Operator side rotating belt units 28 and 30 cooperate to rotate one or more folding fingers 36 around the travel path of the belt units. Diaper 18 can be seen carried by conveyor 20 in an unfolded condition.

Folding fingers 36 are pivotally mounted by pivotal mounts 52 attaching folding one or more folding fingers 36 to both the operator side rotating belt units 28 and 30, and one or more folding fingers 36 to both drive side rotating belt units 32 and 34. Because a folding finger is pivotally mounted at two points to two simultaneously rotating belts (be they operator side rotating belt units 28 and 30, or drive side rotating belt units 32 and 34), during travel with the belts 62 the orientation of folding fingers 36 remains fixed pointing upward for folding fingers 36 carried by the operator side rotating belt units 28 and 30, and fixed pointing downward for folding fingers 36 carried drive side rotating belt units 32 and 34. The distance between the two belts 62 of the operator side rotating belt units 28 and 30 remains constant, and the distance between the two belts 62 of drive side rotating belt units 32 and 34 also remains constant. The operator side rotating belt units 28 and 30 are spaced apart from one another in a cross machine direction at a distance equal to the intended distance for cross-machine direction travel of folding fingers 36 during the folding sequence. The drive side rotating belt units 32 and 34 also are spaced apart from one another in a cross machine direction at a distance equal to the intended distance for cross-machine direction travel of folding fingers 36 during the folding sequence.

Although four folding fingers 36 are shown carried by belts 62 of operator side rotating belt units 28 and 30 and drive side rotating belt units 32 and 34, more or less can be used according to preference. As noted, a single folding finger 36 could be used in the folding operation to fold a single diaper 18, but in a preferred embodiment as shown in FIG. 3B, two folding fingers 36 each act on a single diaper 18, each folding finger 36 extending nearly roughly to a centerline of the diaper 18 in the cross-machine direction.

Figure 4A:
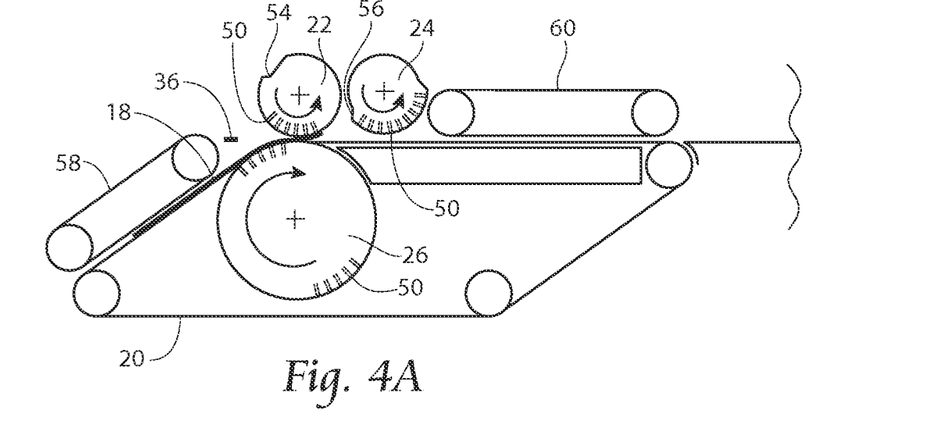
Figure 4B:
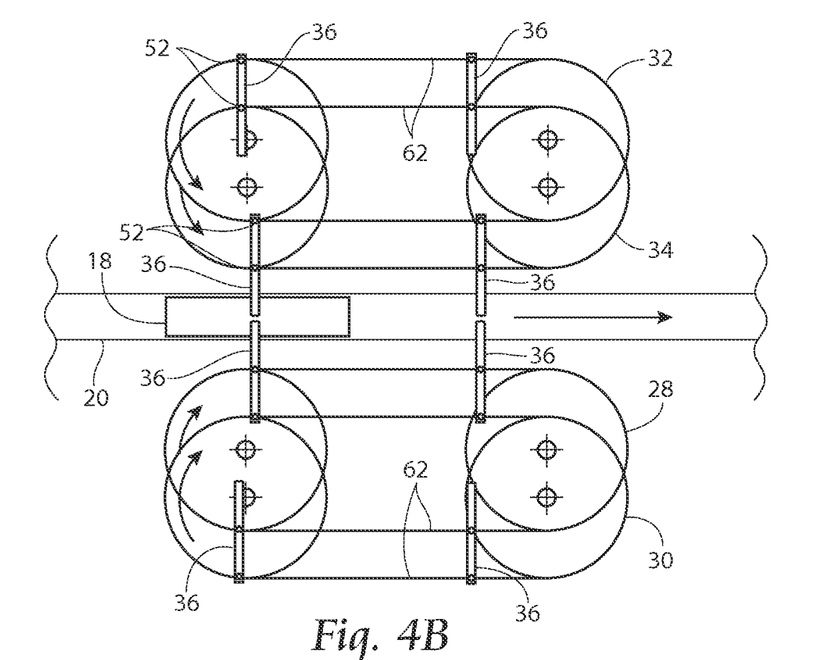

Referring to FIGS. 4A and 4B together as the folding sequence advances, a leading edge of discrete diaper 18 has been picked up by rotating vacuum drum 22 by vacuum ports 50 which are activated as previously described.

Figure 5A:
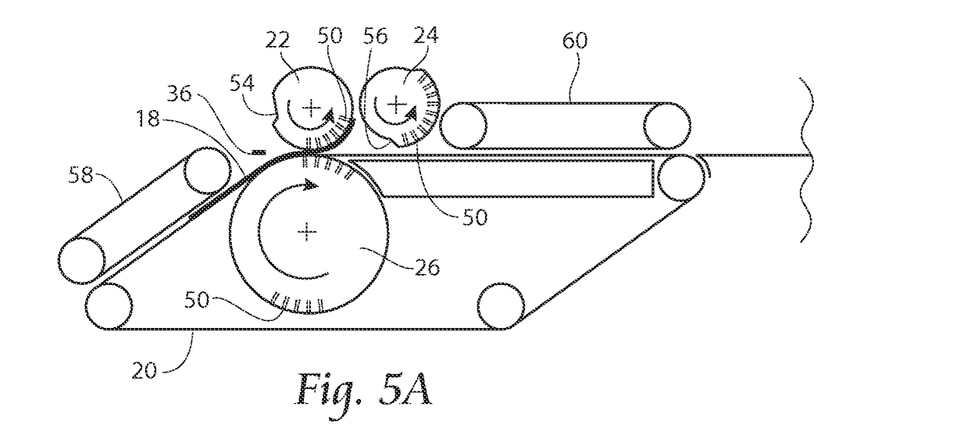
Figure 5B:
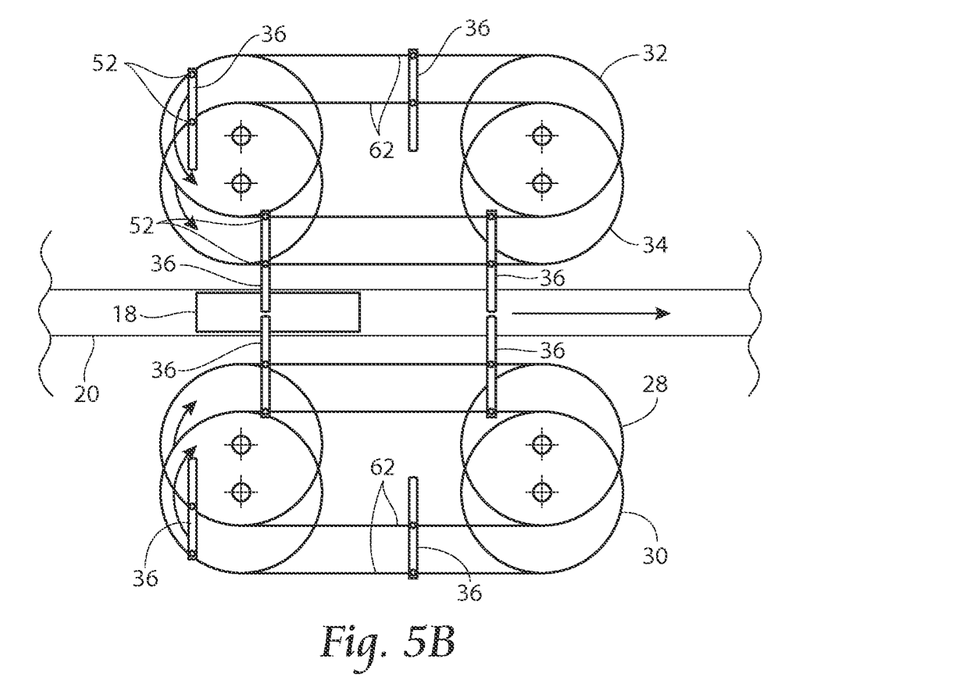

As shown in FIGS. 5A and 5B, rotating vacuum drum 22 has carried the leading edge of diaper 18 further away from rotating drum 26 and conveyor 20, and folding finger 36 approaches a midsection of diaper 18. The folding fingers 36 carried by belts 62 of operator side rotating belt units 28 and 30 and drive side rotating belt units 32 and 34 have advanced accordingly, at preferably about the same speed as the conveyor 20 carrying diaper 18.

Figure 6A:
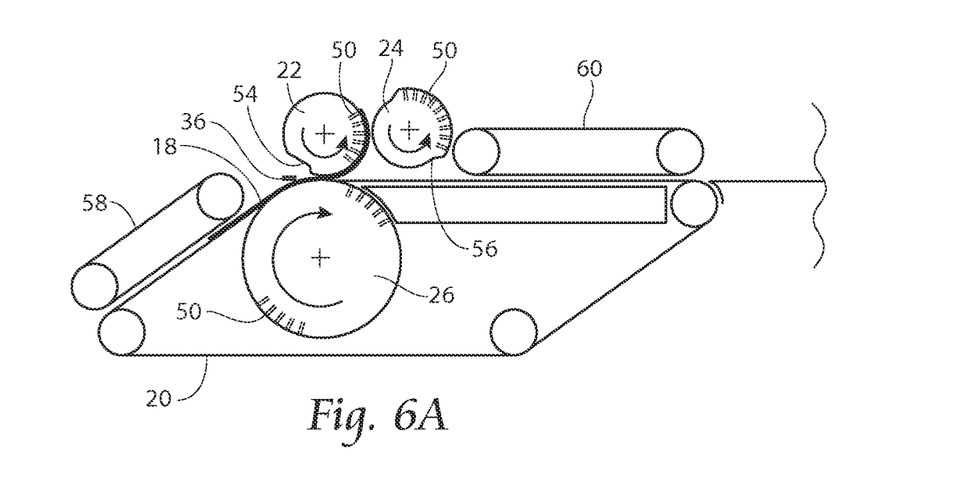
Figure 6B:
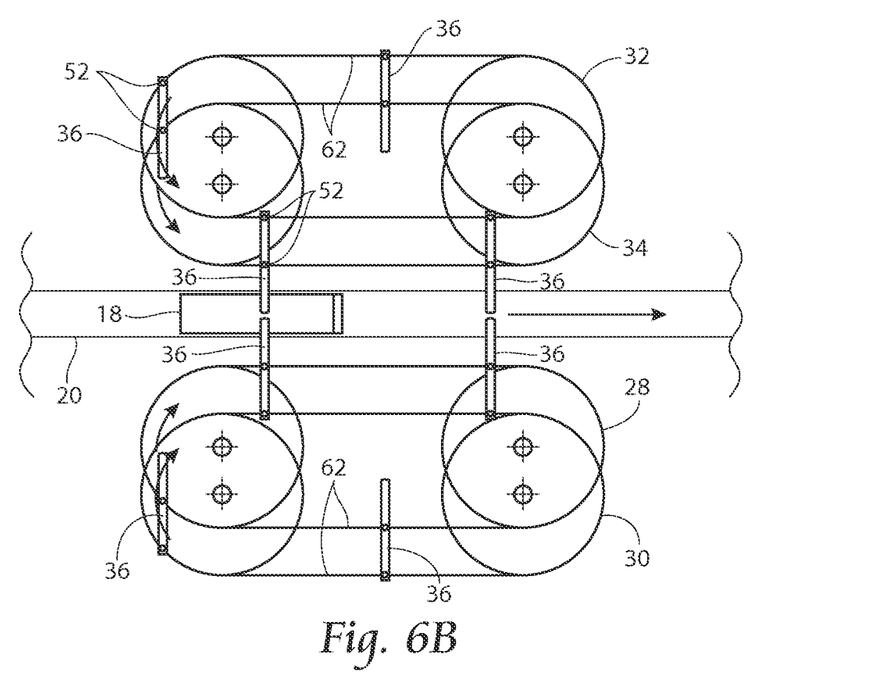

Referring to FIGS. 6A and 6B, folding finger 36 approaches closer to the midsection of diaper 18, and is seen traveling above vacuum drum 26 and about to enter a notched portion 54 of the otherwise cylindrical vacuum drum 22. The notched portion 54 is provided to allow passage of the folding finger 36 past the vacuum drum 22. The folding fingers 36 carried by belts 62 of operator side rotating belt units 28 and 30 and drive side rotating belt units 32 and 34 have advanced accordingly, as shown on FIG. 6B.

Figure 7A:
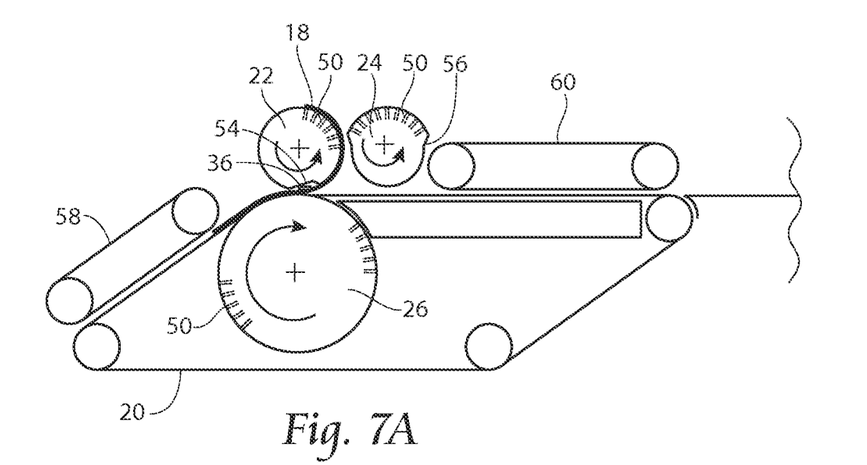
Figure 7B:
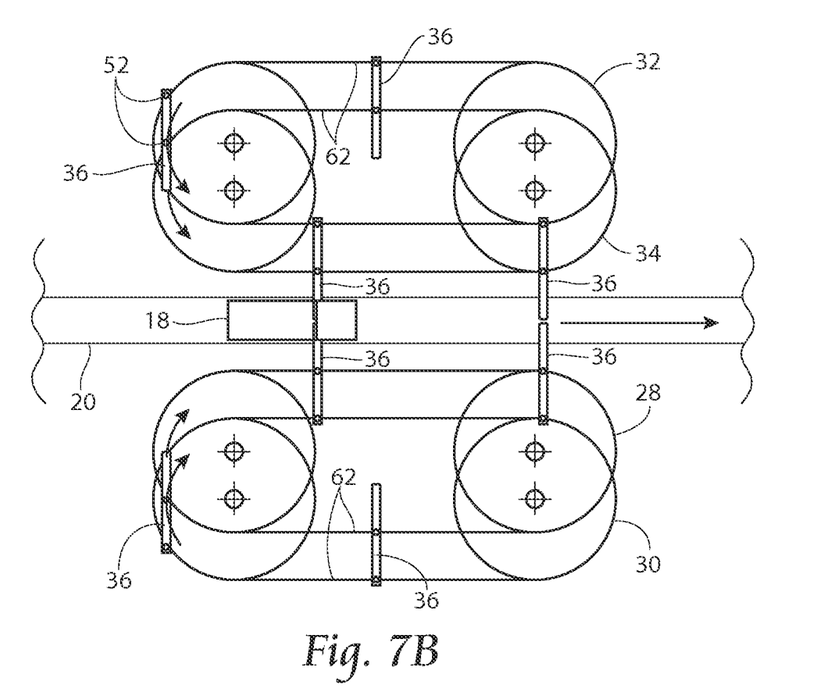

Referring to FIGS. 7A and 7B, folding finger 36 has entered notched portion 54 of the otherwise cylindrical vacuum drum 22 and contacted a midsection of diaper 18 to initiate a fold at the point of contact, while the leading edge of diaper 18 is still carried by rotating vacuum drum 22. The folding fingers 36 carried by belts 62 of operator side rotating belt units 28 and 30 and drive side rotating belt units 32 and 34 have advanced accordingly, as shown on FIG. 7B.

Figure 8A:
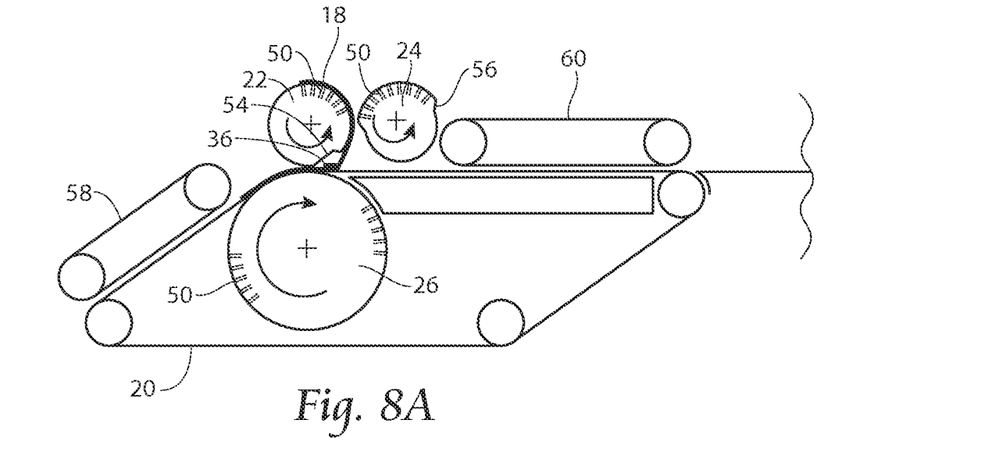
Figure 8B:
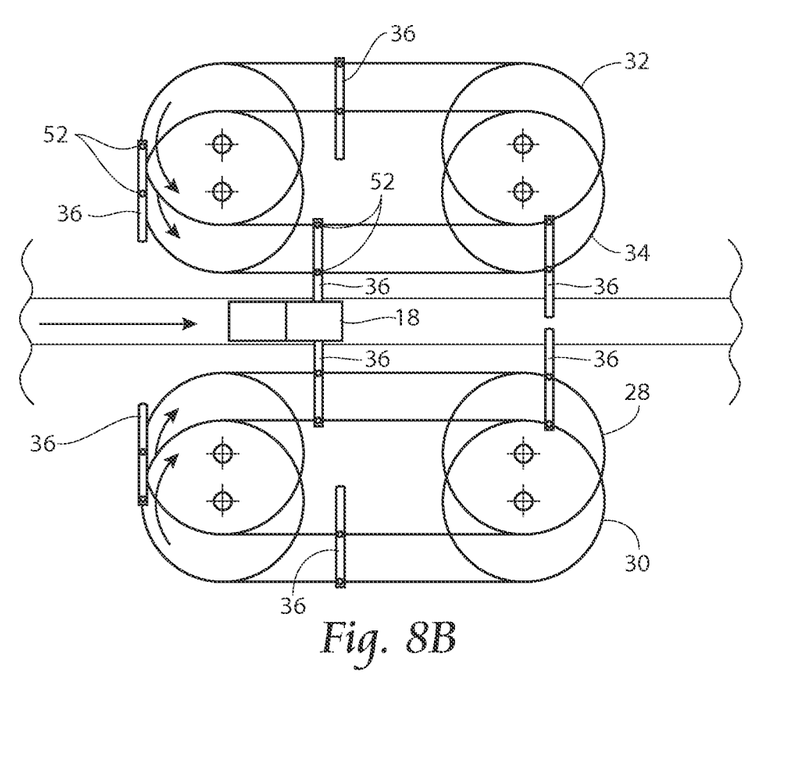

Referring to FIGS. 8A and 8B, folding finger 36 continues its horizontal path just above the top horizontal surface of conveyor 20 and maintains the midsection of diaper 18 on conveyor 20. The folding fingers 36 carried by belts 62 of operator side rotating belt units 28 and 30 and drive side rotating belt units 32 and 34 have advanced accordingly, as shown on FIG. 8B.

Figure 9A:
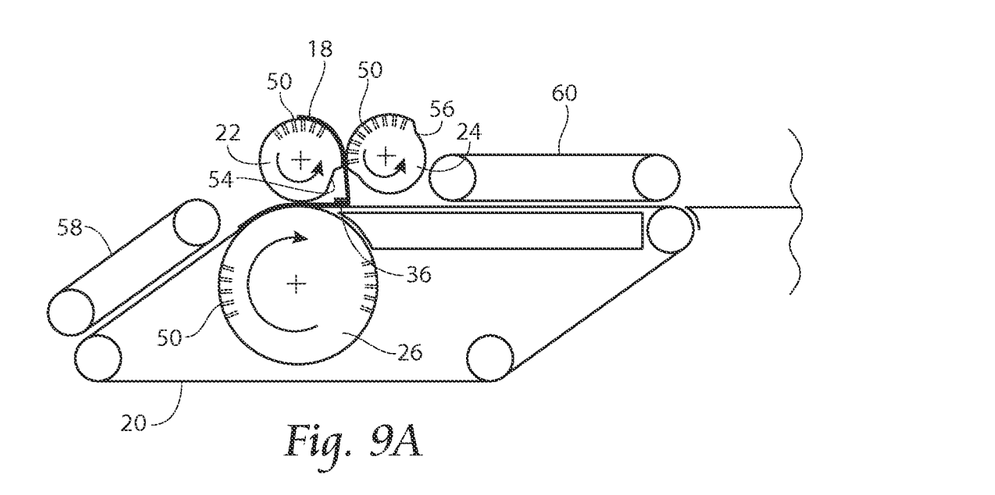
Figure 9B:
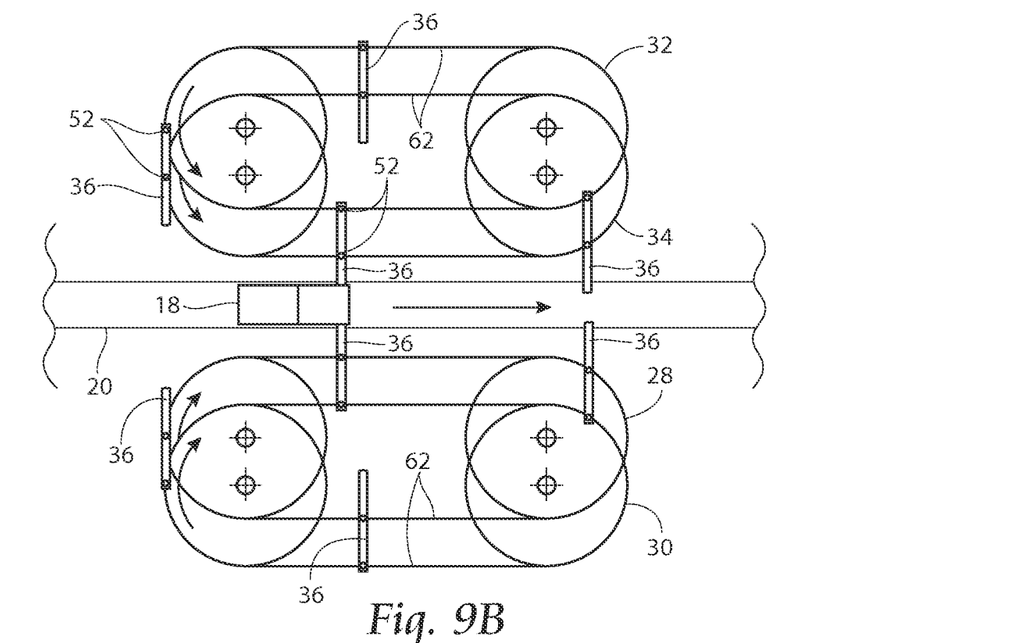

Referring to FIGS. 9A and 9B, vacuum ports 50 on drum 22 have been deactivated past a maximal counterclockwise downstream advance of leading edge of diaper 18, and vacuum ports 50 on drum 24 rotating counterclockwise have been activated. Drum 24 engages what was previously an underside of diaper 18 but has now become a topside of diaper 18. Drums 22 and 24 are closely spaced together at this point in the folding process to maintain control of diaper 18. At points previous to this in the folding process, extended notch 56 creates a non-contacting surface area of drum 24 that has prevented drum 24 from contacting the diaper 18, along drum 22 to carry diaper 18 counterclockwise without interference. The folding fingers 36 carried by belts 62 of operator side rotating belt units 28 and 30 and drive side rotating belt units 32 and 34 have advanced accordingly, as shown on FIG. 9B.

Figure 10A:
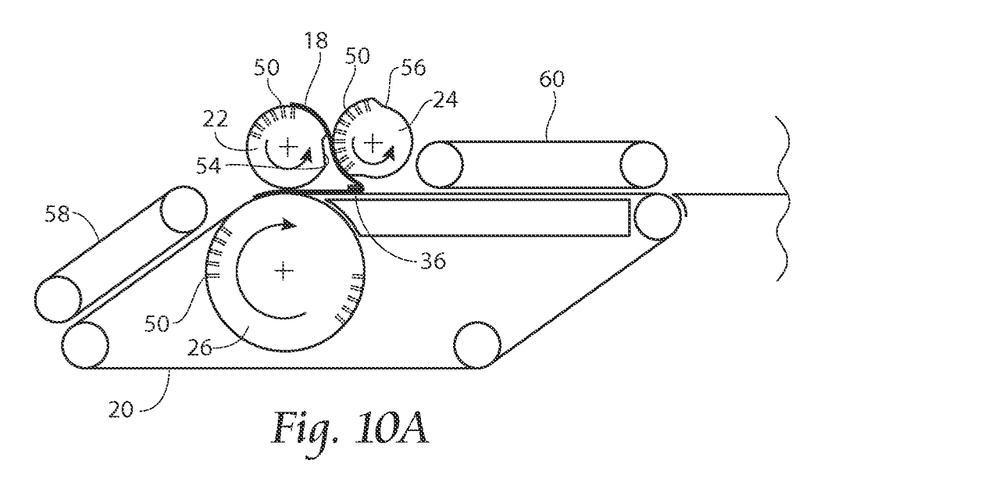
Figure 10B:
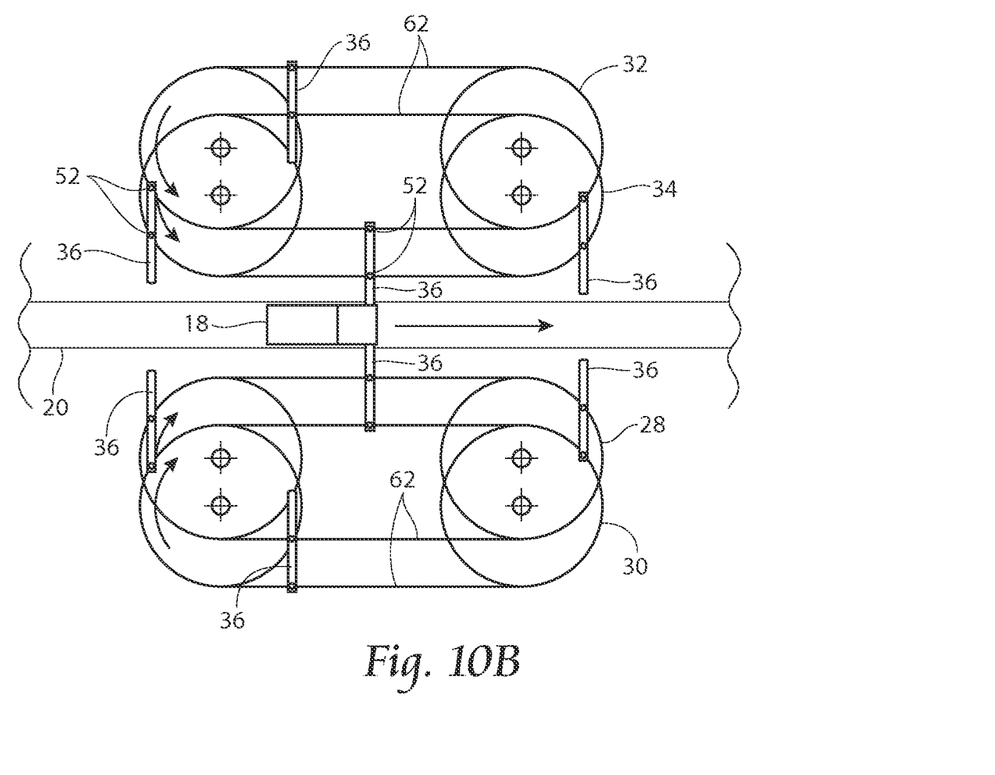
Figures 11A, 11B:
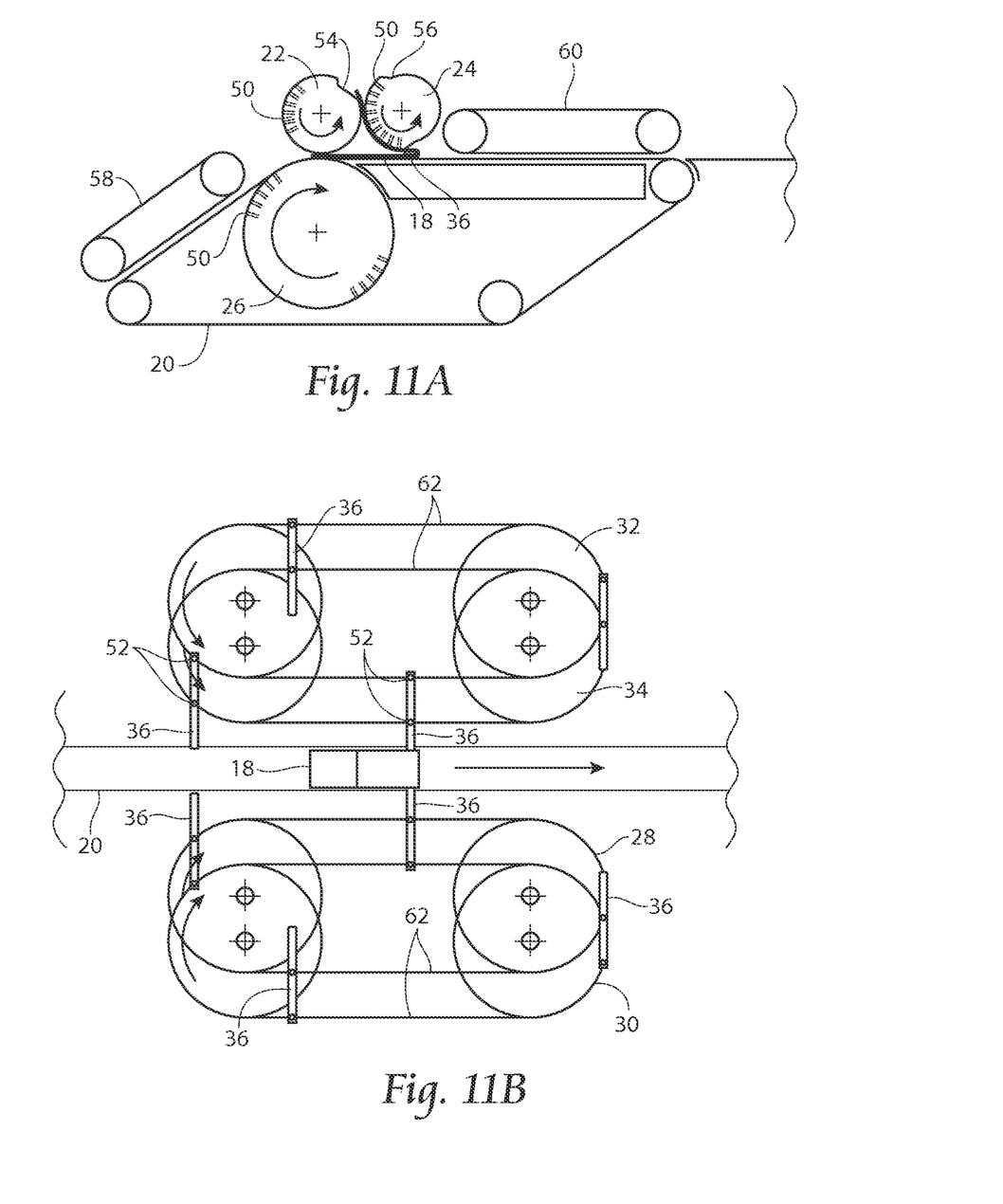
Figure 12A:
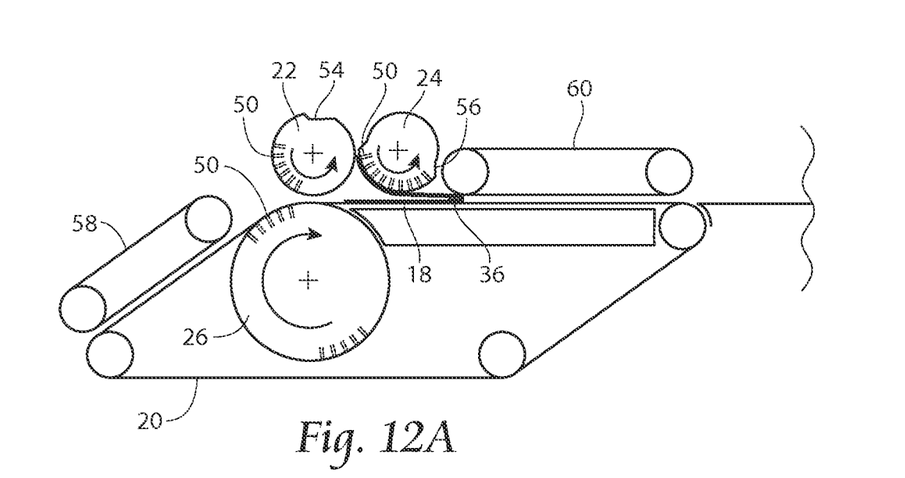
Figure 12B:
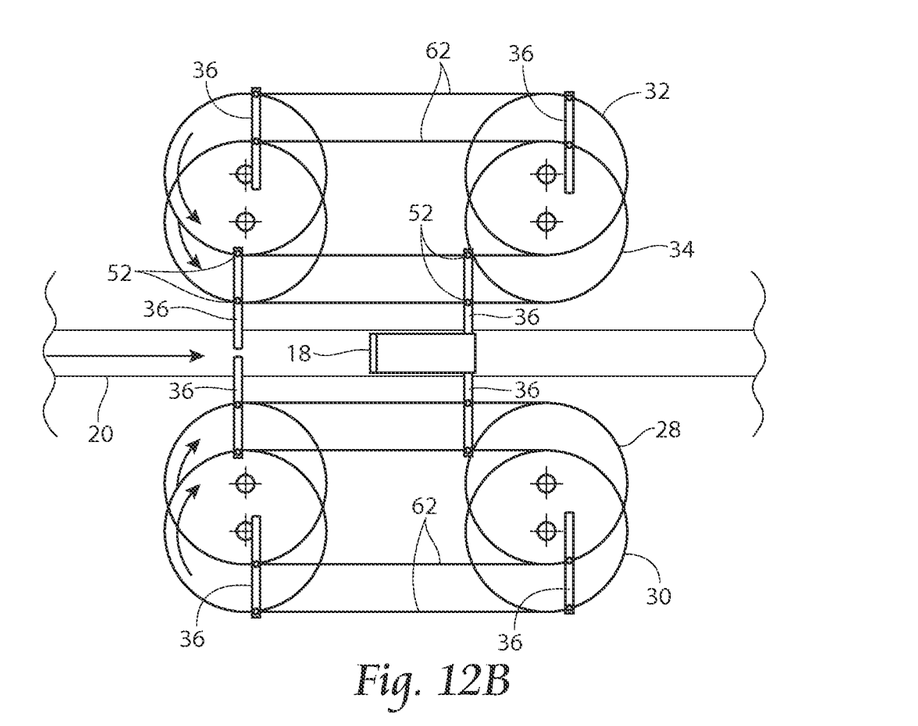

Referring to FIGS. 10A and 10B, drum 24 rotating counterclockwise assists the leading portion of diaper 18 downwards during rotation back towards conveyor 20 to lay the leading half of the diaper over the trailing half of the diaper. The counterclockwise rotational velocity of the outermost perimeter of drum 24 is substantially equal to the speed of conveyor 20, as well as substantially equal to the counterclockwise rotational velocity of the outermost perimeter of drum 22 to avoid shear forces on diaper 18 and to establish a controlled laydown of the leading half of folded diaper 18. The folding fingers 36 carried by belts 62 of operator side rotating belt units 28 and 30 and drive side rotating belt units 32 and 34 have advanced accordingly, as shown on FIG. 10B.

Figure 13A:
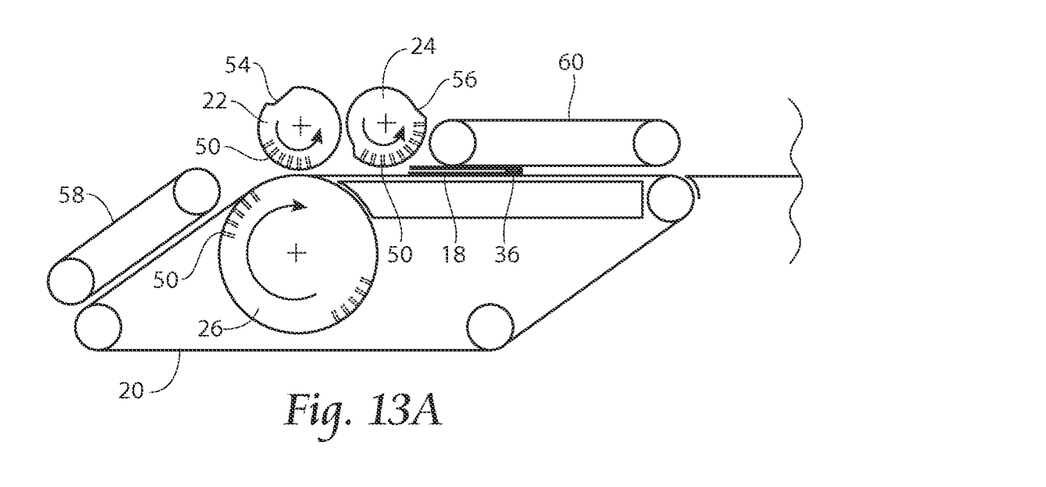
Figure 13B:
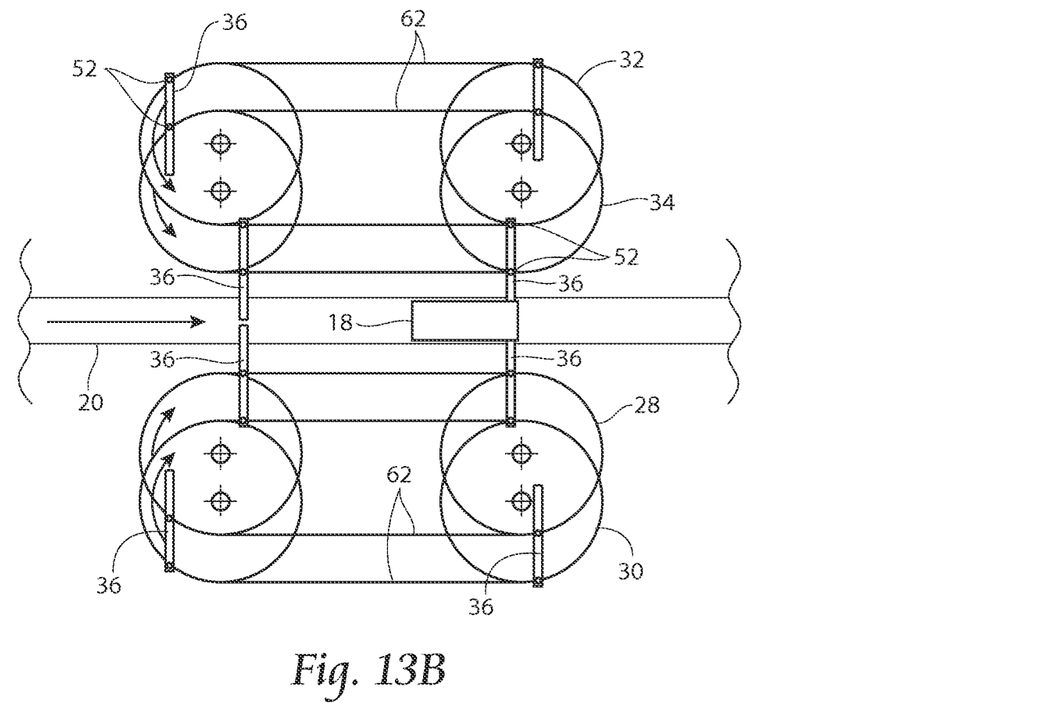

The folding process continues in sequence through FIGS. 11A and 11B, and 12A and 12B, until the fold is completed and the folded diaper 18 is completely folded and the top of diaper 18 is released from vacuum ports 50 of drum 24 as shown in FIG. 13A.

Figure 14A:
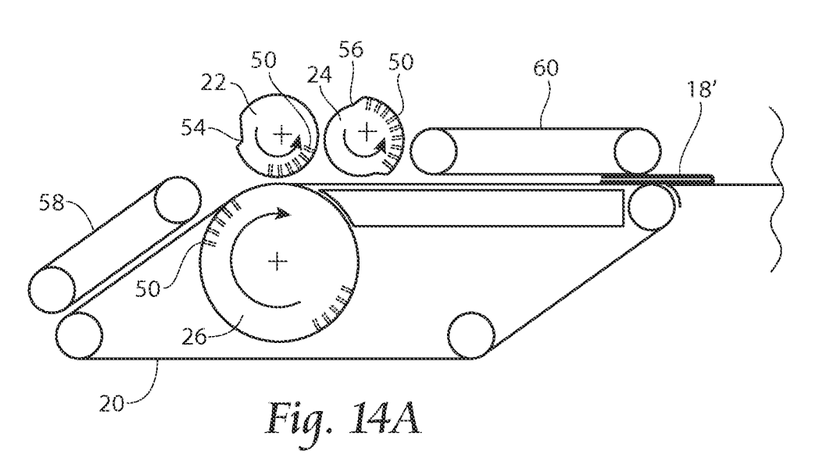
Figure 14B:
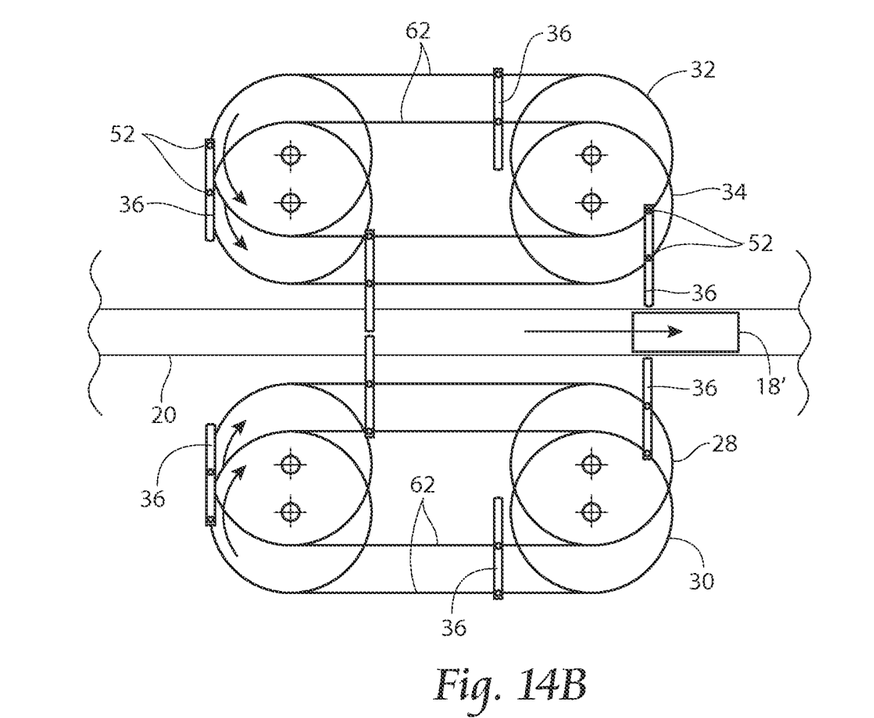

Referring now to FIGS. 14A and 14B, folding fingers 36 round downstream corners of operator side rotating belt units 28 and 30, and drive side rotating belt units 32 and 34 and are thereby withdrawn from the folded diaper 18 in the cross-machine direction, and free to travel along their counterclockwise path until rounding upstream corners of operator side rotating belt units 28 and 30, and drive side rotating belt units 32 and 34 to return to the beginning of the folding process and start anew. Downstream conveyor 60, along with conveyor 20, carry the folded diaper 18' downstream for further processing as desired, such as stacking and packaging.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for folding discrete items, the method comprising:
    conveying an item in a machine direction via a feed conveyor;
    engaging a first side of a leading portion of the item with a first drum positioned adjacent the feed conveyor, the first drum rotating the leading portion in a first rotational direction;
    contacting a folding location of the item with a folding finger oriented in a cross-machine direction and traveling in the machine direction;
    timing movement of the folding finger such that the folding finger is positioned within a notched portion formed in the first drum as the folding finger travels between the first drum and the feed conveyor, so as to allow for passage of the folding finger past the first drum;
    releasing the first side of the leading portion of the item from the first drum;
    engaging a second side of the item with a second drum positioned adjacent the first drum and downstream therefrom in the machine direction, the second drum rotating the item in the first rotational direction; and
    releasing the second side of the leading portion from the second drum to fold the leading portion of the item onto a trailing portion of the item, with the item remaining on the feed conveyor after folding the leading portion onto the trailing portion.

2. The method of claim 1 further comprising withdrawing the folding finger from the item upon folding thereof by moving the folding finger in the cross-machine direction away from the item, the folding finger remaining oriented in the cross-machine direction as it is withdrawn from the item.

3. The method of claim 2 wherein the folding finger rotates about a travel path to travel in the machine direction and in the cross-machine direction, with the folding finger remaining oriented in the cross-machine direction as it rotates about the travel path.

4. The method of claim 3 further comprising operating one or more rotating belt units each carrying a belt to cause the folding finger to rotate about the travel path.

5. The method of claim 1 further comprising controlling the folding finger to travel in the machine direction at a same speed as the feed conveyor.

6. The method of claim 1 wherein engaging the first side of the leading portion of the item with the first drum comprises selectively activating a retaining portion of the first drum having a plurality of vacuum holes formed therein.

7. The method of claim 1 wherein engaging the second side of the item with the second drum comprises selectively activating a retaining portion of the second drum having a plurality of vacuum holes formed therein.

8. The method of claim 7 further comprising:
   deactivating the vacuum holes on the first drum past a maximal counterclockwise downstream advance of the leading portion, so as to release the item from the first drum; and
   activating the vacuum holes on the second drum to engage the item with the second drum.

9. The method of claim 1 further comprising:
   contacting the folding location of the item with a second folding finger oriented in the cross-machine direction and traveling in the machine direction; and
   timing movement of the second folding finger such that the second folding finger is positioned within the notched portion formed in the first drum as the second folding finger travels between the first drum and the feed conveyor, so as to allow for passage of the second folding finger past the first drum.

10. The method of claim 1 further comprising maintaining the trailing portion of the item on the feed conveyor by the folding finger while the leading portion is engaged by the first drum and the second drum.

11. The method of claim 1 wherein folding the item comprises folding a diaper.

12. A machine for folding discrete items, the machine comprising:
   a belt conveyor oriented in a machine direction and having a linear portion for linearly translating an item;
   a first engaging member positioned adjacent to the linear portion of the belt conveyor, the first engaging member rotating in a first direction and comprising a retaining portion configured to engage a leading portion of the item traveling on the linear portion of the belt conveyor;
   a second engaging member positioned adjacent to the linear portion of the belt conveyor and adjacent to the first engaging member downstream in the machine direction, the second engaging member rotating in the first direction; and
   a folding finger oriented in a cross-machine direction and configured to travel in the machine direction adjacent the belt conveyor, such that the folding finger passes through a gap between the first engaging member and the belt conveyor.

13. The machine of claim 12 wherein the first engaging member comprises a drum having a notched portion formed therein, the notched portion allowing passage of the folding finger past the first engaging member as it travels in the machine direction.

14. The machine of claim 12 wherein the first engaging member comprises a plurality of vacuum holes formed in the retaining portion to engage the item, wherein the vacuum holes are selectively activated and de-activated to engage and release the item.

15. The machine of claim 12 further comprising one or more finger rotating units operable to cause the folding finger to rotate about a travel path, with the folding finger remaining oriented in the cross-machine direction as it travels about the travel path.

16. The machine of claim 15 wherein the one or more finger rotating units causes the folding finger to move in the cross-machine direction to withdraw the folding finger from the item as the folding finger travels around a downstream corner of the travel path.

17. The machine of claim 15 wherein the one or more finger rotating units causes the folding finger to travel in the machine direction at a speed equal to a speed of the belt conveyor.

18. The machine of claim 12 wherein a portion of the belt conveyor immediately upstream from the first engaging member in the machine direction is an inclined conveyor, to facilitate engaging of the item by the first engaging member.

19. The machine of claim 12 wherein at least one of the first engaging member and the second engaging member comprises a first portion having a first radius and a second portion having a second radius different from the first radius.

20. A method for folding discrete items, the method comprising:
   conveying an item in a machine direction via a feed conveyor;
   carrying a first side of a leading portion of the item with a first engaging member positioned adjacent the feed conveyor and rotating the leading portion in a first rotational direction;
   contacting a folding location of the item with a folding finger oriented in a cross-machine direction and traveling in the machine direction, the folding finger remaining oriented in the cross-machine direction while traveling on a belt that rotates about an axis perpendicular to a rotational axis of the feed conveyor;
   releasing the first side of the leading portion of the item from the first engaging member;
   carrying a second side of the item with a second engaging member positioned adjacent the first engaging member and downstream therefrom in the machine direction and rotating the item in the first rotational direction; and
   releasing the second side of the leading portion from the second engaging member to fold the leading portion of the item onto a trailing portion of the item.

21. The method of claim 20 further comprising withdrawing the folding finger from the item upon folding thereof by moving the folding finger in the cross-machine direction away from the item.

22. The method of claim 20 further comprising contacting the folding location of the item with a second folding finger oriented in the cross-machine direction, the second folding finger remaining oriented in the cross-machine direction while traveling on a second belt that rotates about an axis perpendicular to the rotational axis of the feed conveyor.

23. The method of claim 20 further comprising controlling the folding finger to travel in the machine direction at a same speed as the feed conveyor.

24. The method of claim 20 wherein the first engaging member comprises a first vacuum drum, and wherein the method further comprises timing movement of the folding finger such that the folding finger is positioned within a notched portion formed in the first vacuum drum as the folding finger travels between the first vacuum drum and the feed conveyor, so as to allow for passage of the folding finger past the first vacuum drum.

\* \* \* \* \*